United States Patent
Liu et al.

(10) Patent No.: US 10,588,585 B2
(45) Date of Patent: **\*Mar. 17, 2020**

(54) SYSTEMS AND METHODS THAT USE MULTI-MODAL IMAGING FOR ENHANCED RESOLUTION IMAGES

(71) Applicant: THE CLEVELAND CLINIC FOUNDATION, Cleveland, OH (US)

(72) Inventors: Yang Liu, Akron, OH (US); Francis A. Papay, Westlake, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/180,396

(22) Filed: Nov. 5, 2018

(65) Prior Publication Data

US 2019/0069861 A1 Mar. 7, 2019

Related U.S. Application Data

(63) Continuation of application No. 15/186,854, filed on Jun. 20, 2016, now Pat. No. 10,143,430.

(Continued)

(51) Int. Cl.
*A61B 6/00* (2006.01)
*A61B 5/00* (2006.01)
(Continued)

(52) U.S. Cl.
CPC .......... *A61B 6/4417* (2013.01); *A61B 5/0035* (2013.01); *A61B 5/0059* (2013.01);
(Continued)

(58) Field of Classification Search
CPC ..... A61B 6/4417; A61B 90/37; A61B 5/0035; A61B 5/0059; A61B 5/0071;
(Continued)

(56) References Cited

U.S. PATENT DOCUMENTS

| 5,371,370 A | 12/1994 | Lightfoot |
| 6,417,797 B1 | 7/2002 | Cousins et al. |

(Continued)

FOREIGN PATENT DOCUMENTS

| WO | 83/02534 A1 | 7/1983 |
| WO | 2012/125811 A1 | 9/2012 |

(Continued)

*Primary Examiner* — Courtney D Thomas
(74) *Attorney, Agent, or Firm* — Tarolli, Sundheim, Covell & Tummino LLP

(57) ABSTRACT

One aspect of the present disclosure relates to a system that can employ multi-modal imaging to provide an image with an enhanced resolution. In some instances, the multi-modal imaging can allow an operator to determine and control a tissue margin without the need for intra-operative tissue pathology. The system can include an imaging system that includes a gamma camera to detect a gamma image and an optical imaging modality to detect an optical image. The system can also include a display device to display an enhanced gamma image created based on a function of the optical image. The enhanced gamma image illustrates a characteristic of a disease in the field of view (e.g., a lymphatic pathway, a sentinel lymph node target, or a satellite disease state).

10 Claims, 5 Drawing Sheets

Related U.S. Application Data

(60) Provisional application No. 62/181,376, filed on Jun. 18, 2015.

(51) Int. Cl.
*A61B 90/00* (2016.01)
*A61B 6/06* (2006.01)

(52) U.S. Cl.
CPC .......... *A61B 5/0071* (2013.01); *A61B 5/0075* (2013.01); *A61B 5/7425* (2013.01); *A61B 6/06* (2013.01); *A61B 6/4258* (2013.01); *A61B 6/4266* (2013.01); *A61B 6/5247* (2013.01); *A61B 90/37* (2016.02); *A61B 6/485* (2013.01); *A61B 6/5205* (2013.01); *A61B 2090/371* (2016.02); *A61B 2090/373* (2016.02); *A61B 2090/376* (2016.02)

(58) Field of Classification Search
CPC ....... A61B 5/7425; A61B 6/06; A61B 6/4258; A61B 6/5247; A61B 2090/371; A61B 2090/373; A61B 2090/376
USPC ...................................... 378/62, 63
See application file for complete search history.

(56) References Cited

U.S. PATENT DOCUMENTS

| | | | |
|---|---|---|---|
| 7,190,991 B2 | 3/2007 | Cable et al. | |
| 7,759,625 B2 | 7/2010 | Frangioni et al. | |
| 7,865,230 B1 | 1/2011 | Sevick-Muraca et al. | |
| 7,919,756 B2 | 4/2011 | Beekman | |
| 7,928,397 B2 | 4/2011 | Barrett et al. | |
| 8,224,427 B2 | 7/2012 | Kopriva | |
| 9,008,758 B2 | 4/2015 | Cable et al. | |
| 10,143,430 B2 * | 12/2018 | Liu | A61B 6/4417 |
| 2004/0152975 A1 * | 8/2004 | Blevis | G01T 1/1603 600/427 |
| 2008/0240535 A1 | 10/2008 | Frangioni et al. | |
| 2010/0030069 A1 | 2/2010 | Peter | |
| 2011/0194747 A1 | 8/2011 | Wieczorek | |
| 2015/0016702 A1 | 1/2015 | Huizenga et al. | |
| 2015/0305701 A1 | 10/2015 | Wendler et al. | |
| 2015/0320375 A1 | 11/2015 | De Jong | |
| 2015/0327831 A1 | 11/2015 | Levin et al. | |

FOREIGN PATENT DOCUMENTS

| | | |
|---|---|---|
| WO | 2014/180658 A1 | 11/2014 |
| WO | 2015/061793 A1 | 4/2015 |
| WO | 2015/163942 A1 | 10/2015 |

* cited by examiner

SYSTEMS AND METHODS THAT USE MULTI-MODAL IMAGING FOR ENHANCED RESOLUTION IMAGES

CROSS-REFERENCE TO RELATED APPLICATIONS

This application is a continuation of U.S. application Ser. No. 15/186,854, filed Jun. 20, 2016, which claims the benefit of U.S. Provisional Application No. 62/181,376, entitled "MULTI-MODAL IMAGING," filed Jun. 18, 2015. Each of the aforementioned applications is hereby incorporated by reference in its entirety.

TECHNICAL FIELD

The present disclosure relates generally to multi-modal imaging and, more specifically, to devices, systems, and methods that can employ multi-modal imaging for enhanced resolution images.

BACKGROUND

A surgical margin defines the visible margin of normal tissue that is removed when diseased tissue is surgically removed. Generally, surgical margins can allow total removal of the diseased tissue while minimizing the removal of normal healthy tissue. For example, when the surgical margin is defined, the presence of satellite disease in tissue surrounding or adjacent to diseased tissue and disease that is propagating through regional lymph vessels and lymph nodes must be taken into consideration.

Historically, surgical margins have been determined based on empirical evidence from a series of patients that illustrates how their tumors propagated both locally and regionally. As data for more patients becomes available, surgical margins have been adjusted accordingly. Alternatively, surgical margins can be determined in situ (e.g., for skin cancer using Mohs surgery). In Mohs surgery, after each tissue removal, the tissue is examined for cancer cells, which informs the decision for additional tissue removal, thereby defining the surgical margin. Surgical margins defined with the Mohs surgery remove less normal tissue and experience fewer disease recurrences. However, Mohs surgery is not cost efficient (e.g., employing multiple ancillary staff, requiring more capital and disposable equipment, and lengthening the intraoperative time). An alternative to Mohs surgery would employ in situ determination of surgical margins in real time, thereby obviating the need for the inefficiencies of Mohs surgery while maintaining or exceeding the sensitivity and specificity of tumor removal.

SUMMARY

The present disclosure relates generally to multi-modal imaging and, more specifically, to devices, systems, and methods that can employ multi-modal imaging for enhanced resolution images. For example, the multi-modal imaging can include a gamma imaging modality and an optical imaging modality and can increase the resolution of the gamma image and/or the optical image as a function of a property of the other imaging modality. The multi-modal imaging can be used to determine surgical margins in situ in real time. Multi-modal imaging is an efficient alternative to traditional methods for determining surgical margins with good sensitivity and specificity of tumor removal, including identifying "disease-in-transit" and regional metastasis.

In one aspect, the present disclosure can include a system that can employ multi-modal imaging to allow an operator to determine and control a tissue margin without the need for intra-operative tissue pathology. The system can include an imaging system to record images in a field of view that includes a portion of a patient's body. The imaging system can produce images recorded by multiple modes. For example, the multiple modes can include gamma imaging (e.g., to record a gamma image) and optical imaging (e.g., to record at least one optical image). The gamma imaging modality can also include at least a collimator. The system can also include a display device to display an enhanced gamma image created based on a function of the optical image. The enhanced gamma image can illustrate a characteristic of a disease in the field of view (e.g., a lymphatic pathway, a sentinel lymph node target, or a satellite disease state).

In another aspect, the present disclosure can include a method for enhancing a resolution of a gamma image. Steps of the method can be performed by a system that includes a processor. A collimator-based optical image of a field of view, a lens-based optical image of the field of view and a gamma image of the field of view can be received. Based on the collimator-based optical image of the field of view and the lens-based optical image of the field of view, a resolution corruption function for optical imaging can be determined. A resolution corruption function for gamma imaging can be approximated based on the resolution corruption function for optical imaging. The resolution of the gamma image of the field of view can be enhanced based on the resolution corruption function for gamma imaging.

In a further aspect, the present disclosure can include a method for enhancing the resolution of a gamma image. The method can include receiving a gamma image, a first optical image, and a second optical image of a field of view of a patient. An enhanced gamma image of the field of view (with a higher resolution than the gamma image) can be created by a system including a processor based on the first optical image and the second optical image. The enhanced gamma image can be displayed to provide intraoperative guidance. In some instances, a wearable device can be worn by a user and used to view the enhanced gamma image and, in some instances, at least one of the optical images. In some instances, the user can be a surgeon or a member of the surgical staff to provide a real time, in situ determination of surgical margins without requiring any inefficient intra-operative tissue pathology.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
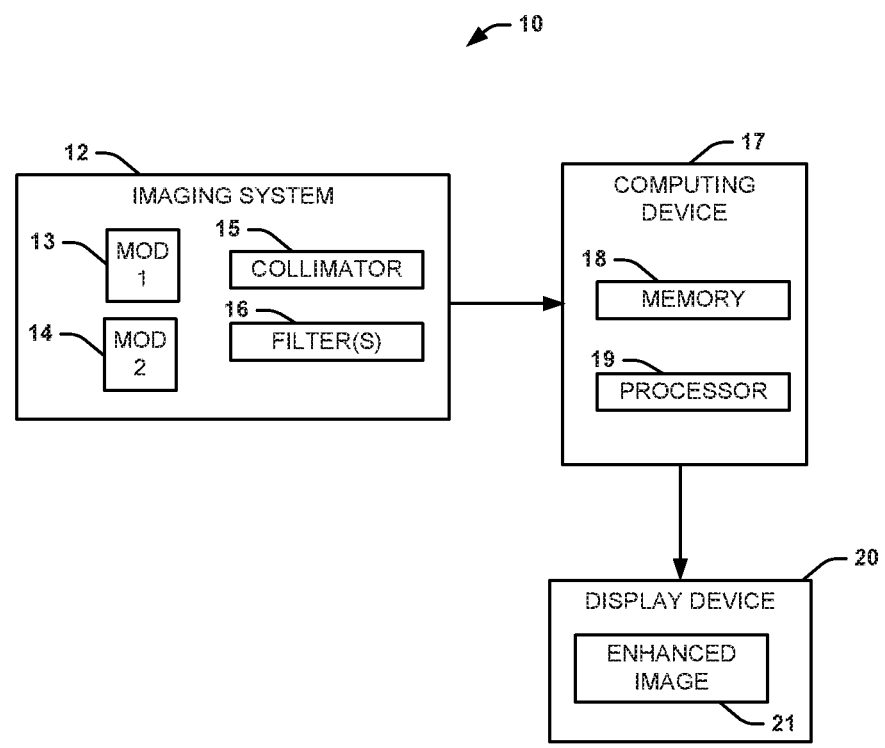
FIG. 1 is a block diagram of an example of a system that can employ multi-modal imaging to create an enhanced image, in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "multi-modal imaging" can refer to the integration of two or more imaging modalities. Examples of imaging modalities can include optical imaging, fluorescence imaging, reflectance imaging, color imaging, light absorption imaging, light scattering imaging, oxygenation saturation imaging, polarization imaging, thermal imaging, infrared imaging, hyperspectral imaging, light field imaging, fluorescence lifetime imaging, bioluminescence imaging, phosphorescence hyperspectral imaging, spectroscopic imaging, chemoluminescence imaging, scintillation imaging, x-ray fluorescence imaging, Cerenkov imaging (to detect Cerenkov luminescence caused by radionuclide decay), etc.

As used herein, the term "surgical margin"' can refer to a definition of the visible margin of normal tissue that is removed when diseased tissue is surgically removed. One example of a surgical margin is a tumor margin.

As used herein, the term "resolution" can refer to the amount of detail visible in an image. In other words, a "high-resolution image" can include a greater amount of detail visible than a "low-resolution image".

As used herein, the term "enhanced" can refer to the resolution of an image being increased so that a low-resolution image becomes a higher-resolution image.

As used herein, the term "goggles" can refer to close-fitting eyeglasses. In some instances, goggles can have side shields.

The term "in situ" is a Latin phrase that translates to "on site" or "in position". Accordingly, as used herein, the term "in situ" can refer to a process (e.g., determining surgical margins) that can occur with bodily tissue still in its place within the body.

As used herein, the term "real time" can refer to a time within a short time (e.g., within a few milliseconds, seconds, or minutes) of the occurrence of an event.

As used herein, the terms "operator" and "user" can refer to an individual conducting a surgical procedure. For example, a user can be a doctor, a nurse, a surgical staff member, a medical student, a medical resident, or the like.

As used herein, the terms "subject" and "patient" can refer, interchangeably, to any warm-blooded organism including, but not limited to, a human being, a pig, a rat, a mouse, a dog, a cat, a goat, a sheep, a horse, a monkey, an ape, a rabbit, a cow, etc.

II. Overview.

The present disclosure relates generally to multi-modal imaging. For example, the multi-modal imaging can include a gamma imaging modality and an optical imaging modality. In some instances, the multi-modal imaging can combine and amplify the strengths of multiple imaging modalities. For example, one imaging modality can have a high resolution and the other imaging modality can have a depth of penetration, but a low resolution. The resolution of the second imaging modality can be increased based on the first imaging modality. Accordingly, the present disclosure relates to devices, systems, and methods that can employ multi-modal imaging for enhanced resolution images.

Multi-modal imaging can find applications to facilitate different types of surgeries. For example, multi-modal imaging can have applications in cancer surgeries, plastic surgeries, cardiovascular surgeries, brain surgeries, and abdominal surgeries. In fact, multi-modal imaging is an efficient alternative to traditional methods for determining surgical margins with good sensitivity and specificity of tumor removal, including identifying "disease-in-transit" and regional metastasis. In fact, the multi-modal imaging can perform an in situ, real time determination of surgical margins, eliminating the cost, time, and personnel inefficiencies of traditional methods for determining the surgical margin while maintaining or exceeding the sensitivity and specificity of tumor removal.

In some instances, the multi-modal imaging can be implemented as goggles that are worn by a user during surgery. The user can identify specific cell types with one imaging modality and simultaneously view transcutaneous lymphatic flow, sentinel lymph nodes of the particular drainage basin of the affected tissue with another imaging modality. This added modality allows the user to view pathways of disease-in-transit in addition to the primary lymph node drainage patterns. The multi-modal goggles can allow the user to determine tumor margin control without the need for intra-operative frozen tissue pathology margin control, while also determining lymphatic pathways, sentinel lymph node targets, and satellite disease states.

III. Systems

One aspect of the present disclosure, as shown in FIG. 1, can include a system 10 that can employ multi-modal imaging to create an enhanced image 21. The system 10 can provide accurate and intuitive intra-operative guidance combining a high resolution imaging modality (e.g., mod 1 13) and a deep depth imaging modality (e.g., mod 2 14). In some instances, the system 10 can be used to perform an in situ determination of surgical margins in real time, reducing the cost, time, and personnel necessary to determine the surgical margin while still maintaining or exceeding the sensitivity and specificity of tumor removal. The system 10 can empower surgeons to perform intra-operative imaging and lymph node mapping, which can allow for identifying disease-in-transit and regional metastasis. Additionally, the system 10 can improve clinical workflow and reduce patient waiting time.

The system 10 can include an imaging system 12, a computing device 15, and a display device 20. The system 10 can be used to visually identify specific disease states in tissue (e.g., diseased tissue vs. normal tissue) at the time of surgery. As an example, the system 10 can be embodied within a surgically-worn goggle that can allow a user to determine a tumor margin without the need for intra-operative frozen tissue pathology while determining lymphatic pathways, sentinel lymph node targets, and satellite disease states.

The imaging system 12 can employ two or more imaging modalities 13, 14. For example, imaging modality 13 can be a high resolution imaging modality (such as an optical camera) while imaging modality 14 can be a deep depth imaging modality (such as a gamma camera). The gamma camera can be a traditional Anger camera, or newer gamma cameras based on CCD, APD, PMT, etc. Additionally, the gamma camera can include one or more collimators. The optical camera may include one or pluralities of image sensors, lenses and filters. In some instances, the optical imaging camera can include the capability for fluorescence and/or color imaging with a lens and filters. In other instances, the imaging setup can include optical imaging and fluorescence imaging. As an example, the optical camera can be implemented as one camera with a filter wheel, different filters can be used for different fluorescence wavelengths, no filter would allow for color imaging. This is the sequential mode imaging. Two cameras (one for fluorescence; one for color) and a beam splitter may also be used. In still other instances, the optical imaging camera can include an X-ray source (e.g., x-ray generators, betarons, linear accelerators, synchrotron source, etc.). However, other optical imaging modalities are within the scope of this disclosure. For example, it should be appreciated that the optical imaging camera may capture other images, one or more types of said images selected from the group consisting of: a fluorescence image, a reflectance image, a color image, a light absorption image, a light scattering image, an oxygenation saturation image, a polarization image, a thermal image, an infrared image, a hyperspectral image, a light field image, a fluorescence lifetime image, a bioluminescence image, a Cerenkov image, a phosphorescence hyperspectral image, a spectroscopic image, a chemoluminescence image, a scintillation image and a x-ray fluorescence image.

The gamma camera can detect images at great depth, but suffers from lower resolution and offers limited image details. On the other hand, types of optical cameras offer higher resolution, but have difficulties penetrating through dense tissues such as bones.

Components of the imaging system 12 can be arranged in one of several configurations with varying complexity. In any configuration, however, the first imaging modality 13 and the second imaging modality 14 can be configured to image the same field of view including a portion of a patient's body.

In one example configuration, the first imaging modality 13 can be set up along side of the second imaging modality 14. The side-by-side setup provides a simple set-up for the imaging. In an example using a gamma camera and an optical camera arranged side-by-side (or generally not concentric), an attenuation of the gamma rays emitted by the gamma camera is low and uniform across the field of view.

In another example configuration, the first imaging modality 13 can be embedded within the second imaging modality 14 so that the two modalities are concentric and share a center point. The embedded setup provides a compact setup for the imaging. Using a gamma camera and an optical camera arranged concentrically, an attenuation of the gamma rays emitted by the gamma camera is non-uniform across the field of view.

It is not necessary for two modalities 13, 14 to be located at the same image plane, given both modalities 13, 14 are planer imaging (projection-based). For example, the mismatch in sizes between a gamma camera (relatively large due to the use of collimator) and an optical camera (small due to the use of lenses) minimize the area within the gamma camera field of view that may be blocked by the fluorescence camera.

As another example, the imaging system 12 can be set up as virtually embedded (e.g., using a mirror without interfering with each other spatially) to achieve the benefits of the compact setup without actually being compact. The virtually embedded setup can ensure low and uniform attenuation of gamma rays across the entire field of view (e.g., the path length of gamma attenuation is uniform).

In a further example, the first imaging modality 13 and the second imaging modality 14 can be situated on different sides of the patient with or without a mirror.

Figure 2:
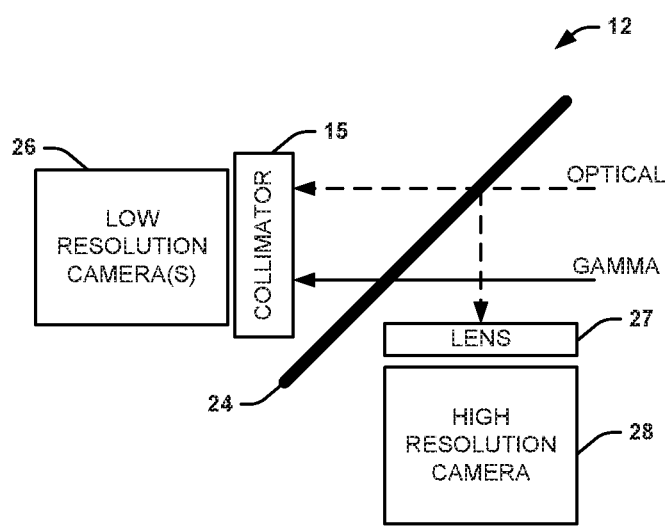
FIG. 2 is a block diagram of an example setup of the imaging system that can be used by the system in FIG. 1.

One example configuration of the imaging system 12, shown in FIG. 2, includes a complementary high-resolution dual modal imaging setup. For example, this setup can include a beam splitter 24, a low resolution camera 26, and a high resolution camera 28. In some instances, the low resolution camera 26 can include a gamma camera and a low resolution portion of an optical camera, while the high resolution camera 28 can include a high resolution portion of the optical camera.

The low resolution camera 26 can be a collimator-based low resolution optical-gamma dual-modal camera that includes one or more collimators 15 (in any of a variety of configurations, such as parallel pinholes, single pinhole, diverging or converging pinholes; coded aperture configuration, or the like). In some instances, the collimator-based low resolution optical-gamma dual-modal camera can include at least one of scintillation crystals, a tunable filter, and a detector (e.g., a photomultiplier tube, a silicon photomultiplier, an avalanche photodiode, a silicon photodiode, or the like). The high resolution camera 28 can include a lens 27 and other components (e.g., one or more filters) to form a lens-based high resolution optical camera.

The beam splitter 24 (e.g., a thin mirror that is optically opaque or partially transparent) can split the optical ray so that a portion of the reflected optical rays are detected by the low resolution optical-gamma dual-modal camera to produce a low resolution optical image and a portion of the reflected optical rays are detected by the high resolution optical camera to produce a high resolution optical image. The reflected gamma rays are detected by the low resolution optical-gamma dual-modal camera. However, the low resolution camera 26 need not be a dual mode camera. Only, the low resolution optical imaging modality and the gamma imaging modality need to have the same type of collimators so that the transfer function of the collimators are the same. Additionally, the lens-based and the collimator-based optical images must be of the same scene captured at the same perspective/angle, so that the same objects are captured at the same projection angle. Additionally, a single tracer labled with both fluorescence and gamma isotope can ensure that both a fluorescence signal and gamma signal are emitted from the same target.

Referring again to FIG. 1, the images detected by the imaging system 12 can be fed to computing device 17 for further processing. The computing device 17 can include at least a non-transitory memory 18 that stores computer-executable instructions and a processor 19 that executes the computer-executable instructions to create the enhanced image 21. The computing device 17 can be, for example, operated in connection with a general purpose computer, special purpose computer, and/or other programmable data processing apparatus. Accordingly, the memory 18 can be any non-transitory medium that is not a transitory signal and can contain or store the program for use by or in connection with the instruction or execution of the processor 19 of a system, apparatus, or device. The memory 18 can be, for example but not limited to, an electronic, magnetic, optical, electromagnetic, infrared, or semiconductor system, apparatus or device. More specific examples (a non-exhaustive list) of the memory 19 can include the following: a portable computer diskette; a random access memory; a read-only memory; an erasable programmable read-only memory (or Flash memory); and a portable compact disc read-only memory. It will be understood that the memory 18 can provide either a temporary data store or a permanent data store.

Figure 3:
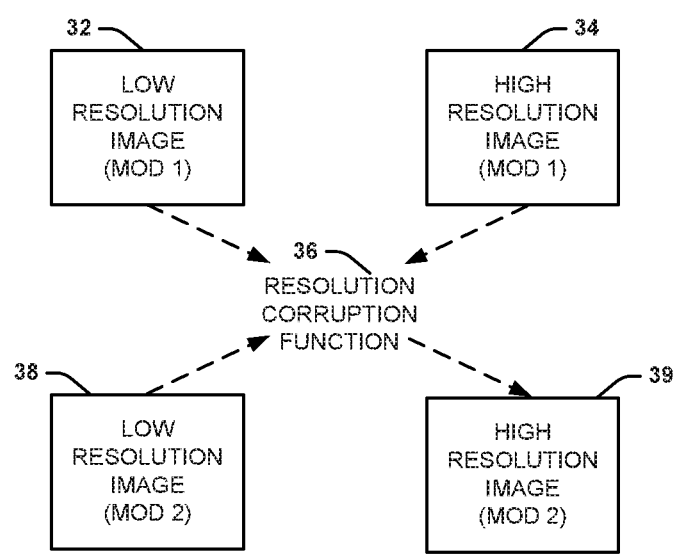
FIG. 3 is an example of the resolution enhancement that can be accomplished by the system in FIG. 1.

In an example, shown in FIG. 3, the images detected by the imaging system 12 can include a low resolution image from one imaging modality 32, a high resolution image from that imaging modality 34 and a low resolution image from a second imaging modality 38. For example, the optical imaging system can be used to produce a low resolution image and a high resolution image, while a gamma imaging modality can be used to produce a low resolution image. The images from the first imaging modality 32, 34 (e.g., the optical imaging modality) can be used to improve a resolution of the low resolution image from the second imaging modality 38 (e.g., the gamma imaging modality). This improvement of the resolution can be based on a certain function of images 32 and 34. For example, the function can be a resolution corruption function 36, which can be determined based on the low resolution image from the first imaging modality 32 and the high resolution image from the first imaging modality 34. The resolution corruption function 36 can be used to approximate a resolution corruption function for the other imaging modality (such as gamma imaging) to reconstruct a high resolution image from the second modality 39 based on the low resolution image from the second modality 38. In some instances, the resolution corruption function for gamma imaging can be approximated as equal to the resolution corruption function for optical imaging.

As an example, the first imaging modality can be an optical image and the second imaging modality can be a gamma image. In some instances, the increased resolution of the gamma image can be a high resolution gamma image with a resolution approximately matching that of the high resolution optical image. The low resolution is primarily due to the inability to use a lens system due to the particle nature of gamma rays (weak wave nature due to high energy of gamma radiation). The imaging system 12 can offer a "lens equivalent" for gamma rays. The gamma lens equivalent can be achieved through a combination of computation and approximation based on the optical imaging counterpart. Essentially, the loss of resolution due to the use of a collimator rather than a lens is calculated with optical imaging. The "loss of resolution" matrix for optical imaging is used to approximate the "loss of resolution" for gamma imaging, assuming there is a "gamma lens" physically possible; therefore, the virtual high resolution gamma images can be reconstructed based on the low-resolution collimator-based gamma image and the transfer function of "gamma lens".

Referring again to FIG. 1, the computing device 17 can be coupled to a display device 20. The display device 20, in some instances, can include a graphical display configured to display at least the enhanced image 21. In some instances, the display device 20 can overlay one of the other images with the enhanced image 21. For example, optical images can be overlaid and registered (e.g., based on fiducial markers, point-based registration, surface-based registration, intensity-based registration, feature-based registration, etc.) with the enhanced image 21 to help the user understand the state of diseases, such as cancer. For example, a transformation model used for the registration may comprise linear transformation, or non-rigid/elastic transformation. Spatial or frequency domain methods may be used, as well as automatic or interactive methods. A computer will be used as needed for computation and image registration. Depth sensors may be used for proper calibration of registration matrix.

One application of such a system is for sentinel lymph node mapping, where one tracer (gamma-fluorescence dual labeled) or multiple tracers (gamma tracers and fluorescence tracers such as inducyanine green) are co-injected to find the nearest lymph nodes. This system may also be applied to image tumors, before, during and post operation. In some instances, the display device 20 can include a conventional display, in which the gamma image and the optical image are represented as a single image. In other instances, the display device 20 can include a picture-in-picture display, in which one of the images is displayed as a picture and the other image is displayed as a thumbnail within the picture.

As an example, the display device can be within surgical goggles or an equivalent user wearable device. The surgical goggles can be coupled to a remote computing device to become a specialized goggle system. At least a portion of the imaging system 12 can be worn by a user as goggles that can display information from the imaging modalities during a surgical procedure. For example, an optical imaging modality can be included within the goggles, while a gamma imaging modality can be an external (e.g., handheld) device and/or a module linked to the goggles.

In some instances, a light source for the optical imaging modality can be worn by the user either as part of the goggles or as an accessory to the goggles. In other instances, the gamma light source for the gamma imaging modality can be from a handheld gamma camera or from an external gamma source. The goggles can be in wireless communication with the remote computing device, which can perform a pathological analysis of the images and provide telemedical consulting. The images can be displayed by the goggles. For example, one of the lenses of the goggles can include functional information from the gamma image and the other of the lenses of the goggles can include 3D functional information from the optical imaging. In some instances, the fields of view can be the same for the imaging modalities. In other instances, the optical imaging modality can have a larger field-of-view than the gamma imaging modality.

IV. Methods

Figure 4:
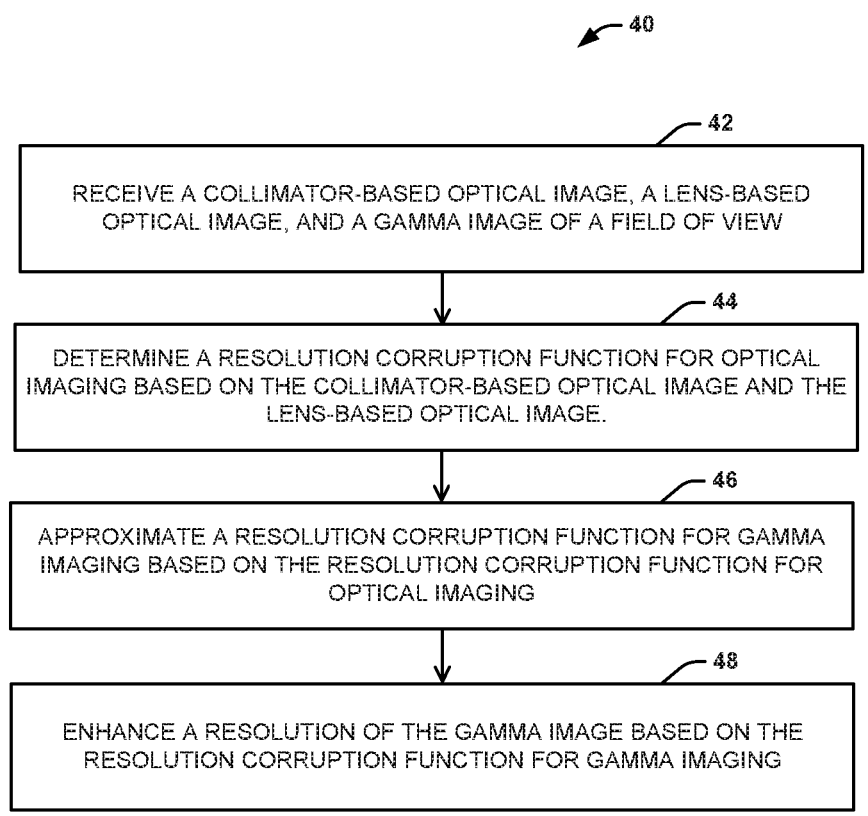
FIG. 4 is a process flow diagram of a method for enhancing a resolution of a gamma image, in accordance with another aspect of the present disclosure.
Figure 5:
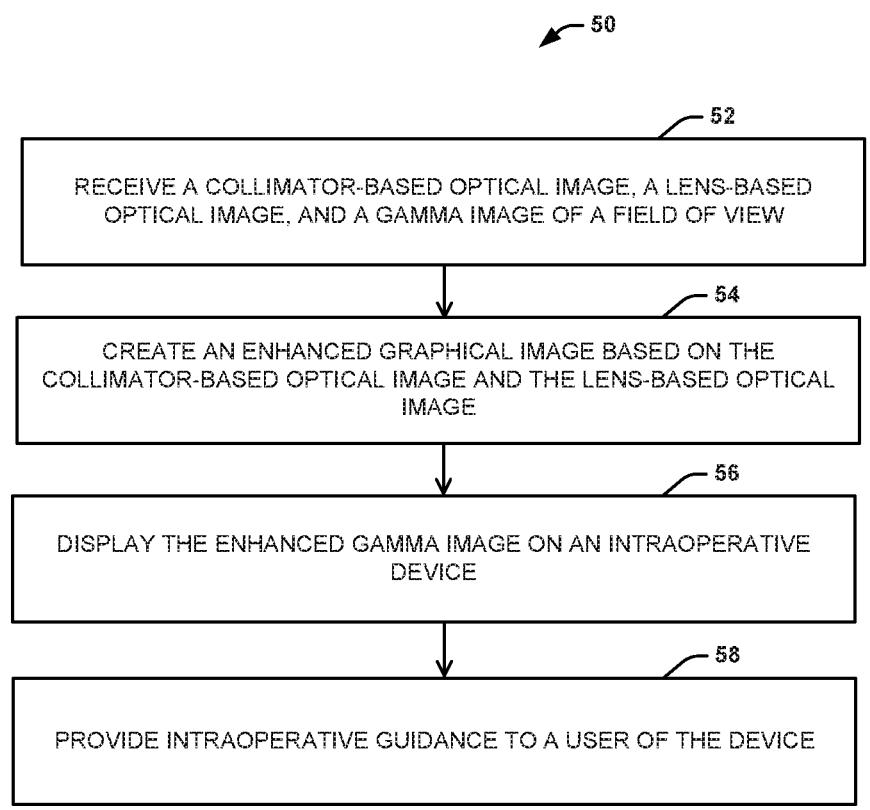
FIG. 5 is a process flow diagram of a method for intra-operative image guidance, in accordance with another aspect of the present disclosure.

Another aspect of the present disclosure can include methods that can employ multi-modal imaging to create an enhanced image. FIG. 4 is a process flow diagram of a method 40 for enhancing a resolution of a gamma image, while FIG. 5 is a process flow diagram of a method 50 for intraoperative image guidance. The methods 40 and 50 can be implemented using the system 10 as shown in FIG. 1, for example.

The methods 40, 50 are illustrated as process flow diagrams with flowchart illustrations. For purposes of simplicity, the methods 40, 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40, 50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 40, 50 may be embodied in hardware and/or in software (including firmware, resident software, microcode, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device. As an example, either of the methods 40, 50 can be stored in a non-transitory memory of a computing device and executed by a processor of the computing device and/or another computing device.

Referring now to FIG. 4, illustrated is a method 40 for enhancing a resolution of a gamma image. At 42, a collimator-based optical image, a lens-based optical image, and a gamma image of a field of view can be received. In some instances, the field of view can include at least a portion of a diseased area of a patient. For example, the diseased area can include a tumor.

At 44, a resolution corruption function for optical imaging can be determined based on the collimator-based optical image and the lens-based optical image. The collimator-based optical image can have a lower resolution than the lens-based optical image. Additionally, the gamma image can also have a lower resolution than the lens-based optical image. Accordingly, the collimator-based optical image and the gamma image can be referred to as low resolution images, while the lens-based optical image can be referred to as a high resolution image.

At 46, a resolution corruption function for gamma imaging can be approximated based on resolution corruption function for optical imaging. In some instances, the resolution corruption function for gamma imaging can be approximated as equal to the resolution corruption function for optical imaging. At 48, a resolution of the gamma image can be increased based on the resolution corruption function for gamma imaging. The imaging modality using both optical and gamma imaging can increase the resolution of the gamma image. Accordingly, by combining both optical imaging and gamma imaging, the strengths of both imaging modalities can be increased.

Additionally, in another method, the aforementioned instruments can be used in combination with imaging contrast agents. In some instances, the instruments in conjunction with florescence-gamma dual labeled contrast agents. In other instances, the instruments can be used in conjunction with optical-gamma dual labeled contrast agents (other than using fluorophores). In other instances, the instruments can be used in conjunction with fluorescence-X-ray dual labeled contrast agents In further instances, the instruments can be used in conjunction with optical-X-ray dual labeled contrast agents (other than using fluorophores). In still other instances, the instruments can be used in conjunction with co-injection of multiple contrast agents. (co-injection of fluorescence and gamma tracers; co-injection of fluorescence and x-ray contrast agents; co-injection of other optical tracers with radionuclides and/or x-ray tracers) The tracers aforementioned may be small molecule based, peptide-based, antibody-based or nanoparticle-based; they may be organic or inorganic in nature. Examples of applications of these methods include sentinel lymph node mapping, tumor imaging, angiography, etc.

Referring now to FIG. 5, illustrated is a method 50 for intraoperative image guidance. At 52, a collimator-based optical image, a lens-based optical image, and a gamma image of a field of view can be received. At 54, an enhanced graphical image can be created based on the collimator-based optical image and the lens-based optical image. At 56, the enhanced gamma image can be displayed on an intraoperative device (e.g., a wearable device, such as goggles). At 58, intraoperative guidance can be provided to a user of the device.

From the above description, those skilled in the art will perceive improvements, changes and modifications. Such improvements, changes and modifications are within the skill of one in the art and are intended to be covered by the appended claims.

The invention claimed is:

1. A system comprising:
a non-transitory memory storing instructions; and
a processor to access the memory and execute the instructions to:
receive a collimator-based optical image of a field of view related to a patient, a lens-based optical image of the field of view, and a gamma image of the field of view;
determine a resolution corruption function for optical imaging based on the collimator-based optical image of the field of view and the lens-based optical image of the field of view;
approximate a resolution corruption function for gamma imaging based on the resolution corruption function for optical imaging; and
enhance a resolution of the gamma image of the field of view based on the resolution corruption function for gamma imaging.

2. The system of claim 1, wherein the collimator-based optical image of the field of view is a low-resolution image and the lens-based optical image of the field of view is a high-resolution image.

3. The system of claim 1, wherein the gamma image of the field of view is a low resolution image.

4. The system of claim 1, wherein the resolution corruption function for gamma imaging is approximated as equal to the resolution corruption function for optical imaging.

5. The system of claim 1, wherein the optical images are produced by an optical imaging modality and the gamma image is produced by a gamma imaging modality.

6. The system of claim 1, wherein the collimator-based optical image and the lens-based optical image of the field of view are formed by splitting an optical beam at a beam splitter to permit collimator-based detection and lens-based detection.

7. A system comprising:
a non-transitory memory storing instructions; and
a processor to access the memory and execute the instructions to:
   receive a gamma image of a field of view of a patient;
   receive a first optical image of the field of view of the patient;
   receive a second optical image of the field of view of the patient;
   create an enhanced gamma image of the field of view based on the first optical image and the second optical image;
   display the enhanced gamma image to provide intraoperative guidance,
   wherein the enhanced gamma image has a greater resolution than the gamma image.

8. The system of claim 7, wherein the first optical image comprises a collimator-based optical image and the second optical image comprises a lens-based optical image.

9. The system of claim 8, wherein the resolution of the gamma image is increased based on a difference between the collimator-based optical image and the lens-based optical image.

10. The system of claim 7, wherein the enhanced gamma image illustrates a characteristic of a disease in the field of view that facilitates the intraoperative guidance.

\* \* \* \* \*